United States Patent [19]

Zwiener et al.

[11] Patent Number: 5,364,955
[45] Date of Patent: Nov. 15, 1994

[54] COMPOUNDS CONTAINING ALKOXYSILANE AND AMINO GROUPS

[75] Inventors: Christian Zwiener; Lutz Schmalstieg; Josef Pedain, all of Cologne, Germany

[73] Assignee: Bayer Aktiengesellschaft, Leverkusen, Germany

[21] Appl. No.: 144,090

[22] Filed: Oct. 27, 1993

[30] Foreign Application Priority Data

Nov. 6, 1992 [DE] Germany ............... 4237468

[51] Int. Cl.$^5$ ............... C07F 7/10
[52] U.S. Cl. ............... 556/418; 556/420; 556/421
[58] Field of Search ............... 556/418, 421, 420

[56] References Cited

U.S. PATENT DOCUMENTS

| 3,033,815 | 5/1962 | Pike et al. | 260/46.5 |
| 3,759,968 | 9/1973 | Berger et al. | 260/448.2 Q |
| 3,940,360 | 2/1976 | Carder | 556/418 X |
| 4,176,124 | 11/1979 | Darms et al. | 556/418 X |
| 5,126,170 | 6/1992 | Zwiener et al. | 427/385.5 |
| 5,189,190 | 2/1993 | Ching et al. | 556/418 |
| 5,236,741 | 8/1993 | Zwiener et al. | 427/385.5 |
| 5,260,467 | 11/1993 | Barnish et al. | 556/418 |

FOREIGN PATENT DOCUMENTS

| 264022 | 12/1989 | European Pat. Off. |
| 2158945 | 5/1973 | Germany . |
| 1190342 | 5/1970 | United Kingdom . |
| 9205212 | 4/1992 | WIPO . |

OTHER PUBLICATIONS

Angew. Chem. 98 (1986) pp. 237–253.

Primary Examiner—Paul F. Shaver
Attorney, Agent, or Firm—Joseph C. Gil; Lyndanne M. Whalen

[57] ABSTRACT

N-alkoxysilylalkyl-aspartic acid esters are prepared by the reaction of equimolar quantities of amino-alkyl alkoxysilanes with maleic or fumaric acid esters. These N-alkoxysilylalkyl-aspartic acid esters are particularly useful as reactants in the preparation of prepolymers containing alkoxysilane and urea groups.

7 Claims, No Drawings

COMPOUNDS CONTAINING ALKOXYSILANE AND AMINO GROUPS

BACKGROUND OF THE INVENTION

The present invention relates to new compounds containing alkoxysilane and secondary amino groups, to a process for their preparation and to the use of the new compounds as reactants for organic polyisocyanates used in the preparation of prepolymers containing alkoxysilane and urea groups.

Hydrolyzable organofunctional silanes are key components for linking conventional polymer chemistry with silicone chemistry. Compounds of technical importance for this purpose are in particular those corresponding to the general formula

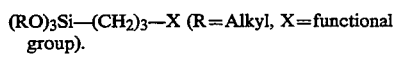

(RO)$_3$Si—(CH$_2$)$_3$—X (R=Alkyl, X=functional group).

Such compounds contain both hydrolyzable silyl groups which cross-link by a "silane polycondensation" in the presence of moisture and other functional groups, X, which enable them to be chemically linked to conventional polymer materials. (See e.g., *Angew. Chem.* 98 (1986) 237–253.)

Hydrolyzable functional silanes corresponding to the above formula in which the functional group X contains Zerewitinoff active H-atoms are potentially capable of modifying polyisocyanates. (See, e.g., WO 92/05212). Commercially available products suitable for this purpose contain NH$_2$ and/or NH groups. SH groups may also be present.

Alkoxysilanes containing SH groups are described, for example, in GB-A-1,102,251; EP-A-O,018,094; DE-A-1,162,818; U.S. Pat. Nos. 3,590,065; 3,849,471; 4,082,790; 4,012,403; and 4,401,286. All alkoxysilanes containing SH groups have the unpleasant odor which is typical of mercaptans. The polymer may, therefore, have an unpleasant odor due to residues of these compounds.

Alkoxysilanes containing amino groups are described, e.g., in *J. Org. Chem.* 36 (1971), p. 3120; DE-A-1,152,695; DE-A-1,271,712; DE-A-2,161,716; DE-A-2,408,480; DE-A-2,521,399; DE-A-2,749,316; U.S. Pat. Nos. 2,832,754; 2,971,864; and 4,481,364. Common to all amino-functional silanes known in the art is the disadvantage of being extremely reactive with isocyanates. These alkoxysilanes can not, therefore, be reacted with polyisocyanates due to the incompatibility, inhomogeneity and extremely high viscosities of the reaction products.

α-Aminoalkyl silane derivatives which can be cross-linked by moisture may be prepared according to German Offenlegungsschriften Nos. 1,812,504 and 1,812,562. The functional silanes described there have, however, failed to achieve technical importance due to the complicated process for their synthesis.

SUMMARY OF THE INVENTION

It is an object of the present invention to provide technically readily available alkoxysilanes containing NH groups.

It is also an object of the present invention to provide alkoxysilanes containing NH groups which may be reacted with isocyanates without the incompatibility, inhomogeneity and viscosity problems encountered with the prior art alkoxysilanes containing NH groups.

It is another object of the present invention to provide a simple, commercially useful process for the production of alkoxysilanes containing NH groups.

These and other objects which will be apparent to those skilled in the art are accomplished by reacting equimolar quantities of amino-alkyl alkoxysilanes represented by a given formula and maleic or fumaric acid esters at a temperature of from about 0° to about 100° C. The product of this reaction, the alkoxysilanes of the present invention are represented by the formula

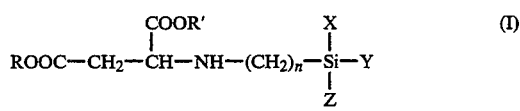

in which R, R', X, Y, Z, and n represent the groups or variables specified below.

DETAILED DESCRIPTION OF THE PREFERRED EMBODIMENTS OF THE PRESENT INVENTION

The present invention relates to compounds containing alkoxysilane and amino groups corresponding to the formula

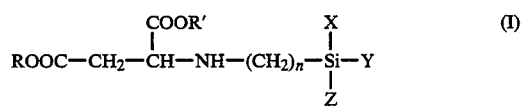

in which
R and R' represent identical or different organic groups which are isocyanate-inert below 100° C.,
X, Y and Z represent identical or different organic groups which are isocyanate-inert below 100° C., with the proviso that at least one of these groups is an alkoxy group, and
n represents an integer of from 2 to 4.

The present invention also relates to a process for the preparation of compounds containing alkoxysilane and amino groups represented by formula I in which equimolar quantities of aminoalkyl alkoxysilanes corresponding to the formula

and maleic or fumaric acid esters corresponding to the formula

in which R, R', X, Y, Z and n have the meanings indicated above are reacted within the temperature range of from about 0° to about 100° C.

The present invention also relates to a process for the production of prepolymers containing alkoxysilane and urea groups in which a compound represented by formula I is reacted with an organic polyisocyanate.

The preferred variables in each of formulae I, II and III are as follows:
R and R' represent identical or different alkyl groups having 1 to 4 carbon atoms, most preferably a methyl group or ethyl group;

X, Y and Z represent alkyl or alkoxy groups having 1 to 4 carbon atoms, with the proviso that at least one of the groups is an alkoxy group; and n represents 3.

Compounds in which X, Y and Z each represent a methoxy group and compounds in which X represents an alkoxy group having from 1 to 4 carbon atoms and Y and Z represent identical or different alkyl or alkoxy groups having from 1 to 4 carbon atoms are particularly preferred.

The compounds represented by formula I are prepared by reacting aminoalkyl alkoxysilanes corresponding to the formula II with maleic and/or fumaric acid esters represented by formula III.

The reaction of primary amines with maleic or fumaric acid esters is already known in principle from the literature and has been described, e.g. in EP-A-0,403,921; DE-OS 1,670,812; and DE-OS 2,158,945. None of these publications, however, suggests the reaction of alkoxysilane-functional amines with maleic or fumaric acid esters.

Examples of suitable aminoalkyl alkoxy-silanes from which the alkoxysilanes represented by formula I may be produced include: 2-aminoethyl-dimethylmethoxysilane; 3-aminopropyl-trimethoxysilane; 3-aminopropyl-triethoxysilane and 3-aminopropyl-methyl-diethoxysilane. 3-Aminopropyl-trimethoxysilane and 3-aminopropyl-triethoxysilane are particularly preferred.

Examples of suitable maleic or fumaric acid esters include: maleic acid dimethyl ester; maleic acid diethyl ester; maleic acid di-n-butyl ester; and the corresponding fumaric acid esters. Maleic acid dimethyl ester and maleic acid diethyl ester are particularly preferred.

The reaction of the maleic or fumaric acid ester with the aminoalkyl alkoxysilane is carried out within a temperature range of from about 0° to about 100° C. The quantity of acid ester and aminoalkyl alkoxysilane are generally chosen so that the starting compounds are used in a molar ratio of 1:1. The reaction may be carried out with or without a solvent, but the use of a solvent is less preferred. If a solvent is used, dioxane is an example of a suitable solvent. The reaction may, of course, also be carried out with mixtures of different 3-aminoalkyl alkoxysilanes and mixtures of fumaric and/or maleic acid esters.

The compounds of the present invention containing amino and alkoxysilane groups are colorless to pale yellow. They may be used without further purification for the modification of isocyanate group-containing compounds.

The compounds of the present invention are valuable modifying agents for compounds containing isocyanate groups for the purpose of producing prepolymers containing alkoxysilane and urea groups. Such prepolymers may be used, for example, for the production of sealing compounds which can be cross-linked by "silane polycondensation". When used for this purpose, the prepolymers are often used as mixtures with suitable catalysts, such as, dibutyl tin diacetate. Low molecular weight, basic aminoalkyl trialkoxy-silanes, such as, those represented by formula II, accelerate hardening of the prepolymer. These silanes may, therefore, be added in catalytic quantities when the prepolymer is used to produce a sealant.

Having thus described our invention, the following examples are given as being illustrative thereof. All percentages given in these Examples are percentages by weight.

EXAMPLES

Example 1

N-(3-Triethoxysilylpropyl) aspartic acid diethyl ester 221.0 g (1.0 mol) of 3-aminopropyltriethoxysilane were introduced into a standard stirrer apparatus. 172.0 g (1.0 mol) of maleic acid diethyl ester were added dropwise at room temperature over a period of about 4 hours. The exothermic reaction was maintained at about 30° C. by cooling the apparatus in a water bath. Stirring was then continued for a further 8 hours at room temperature. A clear, colorless liquid having a viscosity of about 30 mPa.s (23° C.) was obtained. Base titration showed almost complete conversion. The amine equivalent weight was about 398 g (theory: 393 g).

Example 2

N-(3-Triethoxysilylpropyl)-aspartic acid dimethyl ester 221.0 g (1.0 mol) of 3-aminopropyltriethoxysilane were introduced into a standard stirrer apparatus. 144.0 g (1.0 mol) of maleic acid dimethyl ester were added dropwise at room temperature over a period of about 4 hours. The exothermic reaction was maintained at about 30° C. by water bath cooling. Crystals of fumaric acid dimethyl ester formed from the maleic acid dimethyl ester by base catalyzed transposition were deposited on the wall of the vessel during the reaction and reacted during the after-stirring period of about 16 hours at room temperature. A clear, colorless liquid having a viscosity of about 30 mPa.s (23° C.) was obtained. The amine equivalent weight determined by base titration was about 372 g (theory: 365 g).

Example 3

N-(3-Triethoxysilylpropyl)-aspartic acid di-n-butyl ester 221.0 g (1.0 mol) of 3-aminopropyl-triethoxysilane and 228.0 g (1.0 mol) of maleic acid di-n-butyl ester were reacted by the same procedure used in Example 1. The viscosity of the clear, pale yellow liquid was about 30 mPa.s (23° C). Base titration showed an amine equivalent weight of about 462 g (theory: 449 g).

Example 4

N-(3-Trimethoxysilylpropyl)-aspartic acid dimethyl ester 179.0 g (1.0 mol) of 3-aminopropyl-trimethoxysilane and 144.0 g (1.0 mol) of maleic acid dimethyl ester were reacted by the same procedure used in Example 2. The viscosity of the clear, pale yellow liquid was about 30 mPa.s (23° C.). Base titration showed an amine equivalent weight of about 331 g (theory: 323 g).

Example 5

N-(3-Trimethoxysilylpropyl)-aspartic acid diethyl ester 179.0 g (1.0 mol) of 3-aminopropyl-trimethoxysilane and 172.0 g (1.0 mol) of maleic acid diethyl ester were reacted by the same procedure used Example 1. A clear, colorless product having a viscosity of about 30 mPa.s (23° C.) was obtained. The amine equivalent weight determined by base titration was about 359 g (theory: 351 g).

Example 6

Preparation of an alkoxysilane-functional polyurethane prepolymer 1000 g of a polyether diol with OH number 56 which had been prepared by the propoxylation of propylene glycol were reacted with 174 g of 2,4-tolylene diisocyanate at 80° C. for 6 hours to form a prepolymer. A prepolymer having an NCO content of 3.5% was obtained.

After cooling the reaction mixture to room temperature, 380 g of the adduct of maleic acid diethyl ester and 3-aminopropyl-triethoxysilane from Example 1 were added dropwise at room temperature with vigorous stirring. After stirring for 1 hour at room temperature, the mixture was free from isocyanate groups. The clear, colorless product obtained had a viscosity of 30,000 mPa.s at 23° C.

Example 7

Moisture hardening of the alkoxysilane-functional polyurethane prepolymer from Example 6

100 g of the product from Example 6 were intimately mixed with 0.5 g of dibutyl tin diacetate and 5 g of 3-aminopropyl-triethoxysilane. A film of this material which was applied to a glass plate (layer thickness 1 mm) hardened overnight to an opaque, elastic plastic.

Example 8

Preparation of an alkoxysilane-functional polyurethane prepolymer 2000 g of a polyether diol with OH number 28 which had been prepared by the propoxylation of propyl glycol followed by ethoxylation of the propoxylation product (PO-EO ratio by weight=85:15) were reacted for 7 hours at 80° C. with 174 g of a mixture of 80% by weight of 2,4-toluylene diisocyanate and 20% by weight of 2,6-toluylene diisocyanate. An isocyanate prepolymer having an NCO content of 1.8% was obtained.

After the prepolymer had cooled to room temperature, 380 g of the adduct of maleic acid dimethyl ester and 3-aminopropyl-triethoxysilane from Example 2 were added dropwise at room temperature with vigorous stirring. After further stirring for 1 hour, the mixture was free from isocyanate groups. The clear and colorless product obtained had a viscosity of 28,000 mPa.s/23° C.

Example 9

Moisture hardening of the alkoxysilane-functional polyurethane prepolymer from Example 8

100 g of the product from Example 8 were intimately mixed with 0.5 g of dibutyl tin diacetate, 5 g of 3-aminopropyl-triethoxysilane and 5 g of methyltrimethoxysilane. A film of this material which was applied to a glass plate (layer thickness 1 mm) hardened overnight to an opaque, elastic plastic.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A compound containing alkoxysilane and amino groups represented by the formula

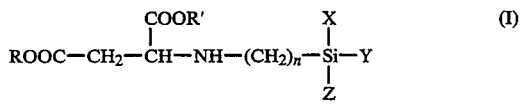

in which
R and R' represent identical or different organic groups that are inert with respect to isocyanate groups at temperatures below 100° C.,
X, Y and Z represent identical or different organic groups which are inert with respect to isocyanate groups at temperatures below 100° C., provided that at least one of these groups is an alkoxy group, and
n represents an integer of from 2 to 4.

2. The compound of claim 1 in which
R and R' represent identical or different alkyl groups having from 1 to 4 carbon atoms,
X represents an alkoxy group having from 1 to 4 carbon atoms,
Y and Z represent identical or different alkyl or alkoxy groups having from 1 to 4 carbon atoms and,
n represents 3.

3. The compound of claim 1 in which
R and R' each represent a methyl or ethyl group,
X, Y and Z each represent a methoxy group and
n represents 3.

4. A process for producing the compounds of claim 1 in which equimolar quantities of amino-alkyl alkoxysilanes corresponding to the formula

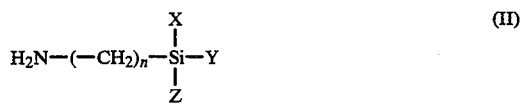

in which
X, Y and Z represent identical of different organic groups which are inert with respect to isocyanate groups at a temperature below 100° C., provided that at least one of these groups is an alkoxy group, and
n represents an integer of from 2 to 4, and a maleic or fumaric acid ester corresponding to the formula

in which
R and R' represent identical or different organic groups which are inert with respect to isocyanate groups at temperatures below 100° C. are reacted within the temperature range of from about 0° to about 100° C.

5. The process of claim 4 in which
R and R' represent identical or different alkyl groups having from 1 to 4 carbon atoms,
X represents an alkoxy group having from 1 to 4 carbon atoms,
Y and Z represent identical or different alkyl or alkoxy groups having from 1 to 4 carbon atoms, and
n represents 3.

6. The process of claim 4 in which
R and R' each represents a methyl or ethyl group,
X, Y and Z each represent a methoxy group, and
n represents 3.

7. A process for the preparation of prepolymers containing alkoxysilane and urea groups comprising reacting the compound of claim 1 with a polyisocyanate.

* * * * *